(12) United States Patent
Callede et al.

(10) Patent No.: US 9,888,908 B2
(45) Date of Patent: Feb. 13, 2018

(54) DEVICE FOR TAKING AT LEAST ONE SAMPLE OF TISSUE

(71) Applicant: COLOPLAST A/S, Humlebaek (DK)

(72) Inventors: David Callede, Sarlat la Caneda (FR); Laurent Pivard, Dortan (FR); Denis Pinaud, Draillant (FR); Fabrice Teppe, Oyonnax (FR); Adrien Moine, Evian (FR)

(73) Assignee: Coloplast A/S, Humlebaek (DK)

( * ) Notice: Subject to any disclaimer, the term of this patent is extended or adjusted under 35 U.S.C. 154(b) by 534 days.

(21) Appl. No.: 14/369,201

(22) PCT Filed: Jan. 11, 2013

(86) PCT No.: PCT/EP2013/050457
§ 371 (c)(1),
(2) Date: Jun. 27, 2014

(87) PCT Pub. No.: WO2013/107693
PCT Pub. Date: Jul. 25, 2013

(65) Prior Publication Data
US 2015/0032026 A1 Jan. 29, 2015

(30) Foreign Application Priority Data

Jan. 16, 2012 (EP) .................................... 12290016

(51) Int. Cl.
*A61B 10/02* (2006.01)
(52) U.S. Cl.
CPC ...... *A61B 10/0266* (2013.01); *A61B 10/0275* (2013.01); *A61B 2010/0208* (2013.01)
(58) Field of Classification Search
CPC ............ A61B 10/0275; A61B 10/0208; A61B 2010/0208

(Continued)

(56) References Cited

U.S. PATENT DOCUMENTS 4,699,154 A * 10/1987 Lindgren ........... A61B 10/0275
600/567
4,958,625 A 9/1990 White
(Continued)

FOREIGN PATENT DOCUMENTS

WO 9639941 A2 12/1996
WO 0154574 A1 8/2001
WO 0224077 A1 3/2002

*Primary Examiner* — Daniel Cerioni
*Assistant Examiner* — Yasmeen S Warsi
(74) *Attorney, Agent, or Firm* — Coloplast Corp., Coloplast A/S; Nick Baumann

(57) ABSTRACT

This invention relates to a device (10) for taking at least one sample of soft tissue from an organ, said device comprising a body (11) and a needle (12) formed by a stylet (13) and a cannula (14) coaxial with said stylet, said device comprising a mechanism for arming the needle, designed for sequentially moving the cannula (14) and then the stylet (13) from a rest position wherein the stylet and the cannula are extended towards the outside of the body, to a shooting position wherein the stylet and the cannula are retracted towards the rear of the body, and a triggering mechanism designed to release the stylet then the cannula and to allow their displacement from the shooting position to the rest position, the cannula being coupled kinematically to a cannula slider (24) comprising at least one retaining element (26) for maintaining the cannula slider in a shooting position, the stylet being coupled kinematically to a stylet slider (30) comprising at least one retaining element (32) for maintaining the stylet slider in a shooting position and means for unlocking (34) the cannula slider. The device is characterized in that at least one element among said retaining element of the cannula slider (26) and said retaining element of the stylet slider (32) comprises at least one hook (50, 50') arranged to cooperate with a retaining device (27, 33) of said hook. The device for taking a sample further (Continued)

includes unlocking means (34, 41) of said arranged hook to release said retaining element from the corresponding retaining device. The sampling device further includes at least one locking element (52, 52', 52", 52''') arranged to prevent said hook to be released from said corresponding retaining device when said locking element is in a locking position and in order to allow said hook to be released from said corresponding retaining device when said locking element is in a position allowing the shot.

19 Claims, 3 Drawing Sheets

(58) Field of Classification Search
USPC .......................................................... 600/567
See application file for complete search history.

(56) References Cited

U.S. PATENT DOCUMENTS

| | | | | |
|---|---|---|---|---|
| 5,797,940 | A * | 8/1998 | Mawhirt | A61B 17/32093 |
| | | | | 606/167 |
| 5,842,999 | A | 12/1998 | Jacobs | |
| 2004/0068231 | A1* | 4/2004 | Blondeau | A61B 10/0275 |
| | | | | 604/157 |
| 2006/0089565 | A1* | 4/2006 | Schramm | A61B 10/0275 |
| | | | | 600/568 |

* cited by examiner

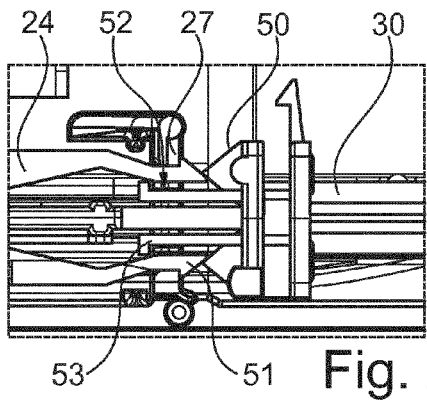
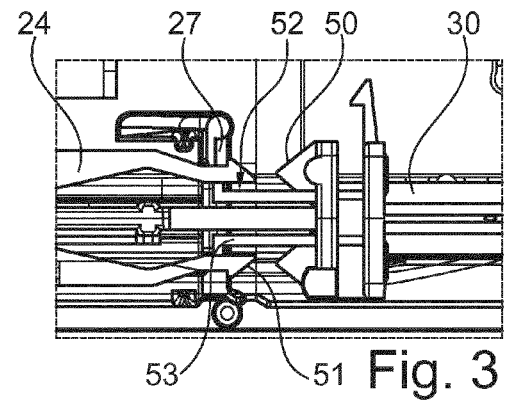
Fig. 2    Fig. 3
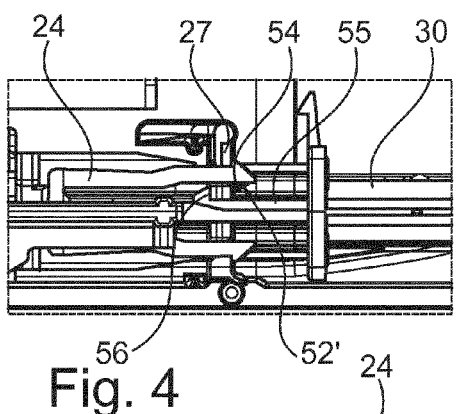
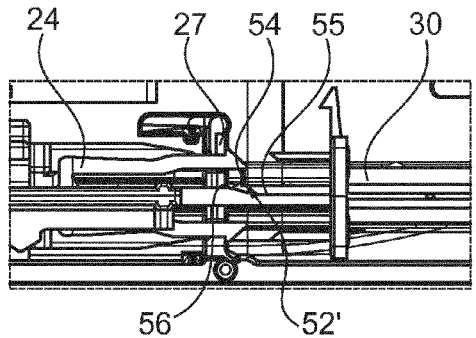
Fig. 4    Fig. 5
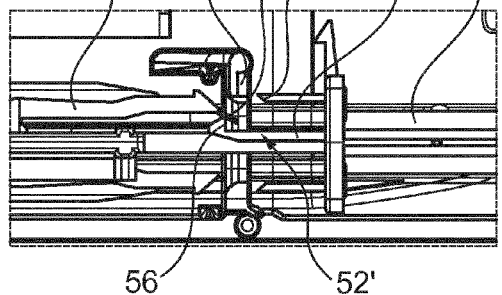
Fig. 6
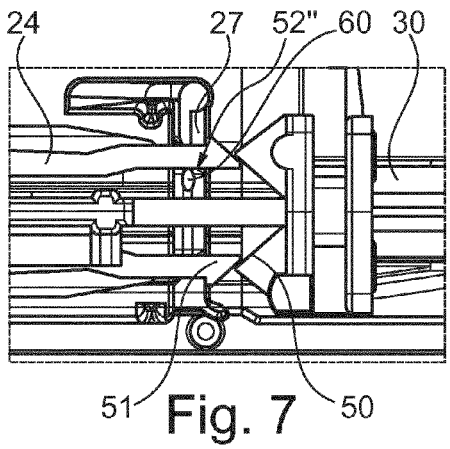
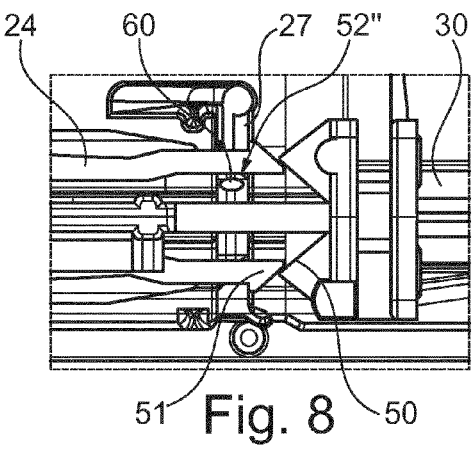
Fig. 7    Fig. 8

DEVICE FOR TAKING AT LEAST ONE SAMPLE OF TISSUE

TECHNICAL FIELD

The present invention relates to a device for taking at least one sample of soft tissue from an organ, said device comprising a body and a needle formed by a stylet and a cannula coaxial with said stylet, said device comprising a mechanism for arming the needle, designed for sequentially moving the cannula and then the stylet from a rest position wherein the stylet and the cannula are extended towards the outside of the body, to a shooting position wherein the stylet and the cannula are retracted towards the rear of the body, and a triggering mechanism designed to release the stylet then the cannula and to allow their displacement from the shooting position to the rest position, the cannula being coupled kinematically to a cannula slider comprising at least one retaining element for maintaining the cannula slider in a shooting position, the stylet being coupled kinematically to a stylet slider comprising at least one retaining element for maintaining the stylet slider in a shooting position and means for unlocking the cannula slider.

BACKGROUND ART

Nowadays, there are several devices for taking samples of soft tissue, these devices being generally used to extract, in a minimally invasive way, a sample of an organ from a human or an animal for analysis purpose. This extraction operation is generally known as biopsy and the used device is known as a biopsy gun.

Such a sampling device comprises in particular a sampling needle formed by a cannula and a stylet, an arming mechanism placed on a body and a trigger also placed on the body of the device.

The arming mechanism is used to partially retract the needle towards the inside of the body of the device, the device is placed near the organ from which one wishes to take a sample, then the trigger is pressed so that the needle can penetrate into the organ. The needle being formed by a stylet and by a cannula, the stylet penetrates into the organ, the cannula then covers the stylet. This stylet comprises at least one notch receiving the tissue to be taken. When the cannula covers the stylet, the tissue sample is trapped in the notch and is cut. The unit is withdrawn so that the sample(s) arranged between the stylet and the cannula can be taken. An example of application of such a device is taking tissues of the prostate.

The arming of the needle is generally achieved in two phases, namely the arming of the cannula in a first phase and the arming of the stylet in a second phase.

During sampling of tissues, it is frequent that the person who carries out the sampling has only one free hand, the other hand being used to hold other medical devices such as for instance an echographic probe. In this case, it is important to be able to manipulate the sampling device with one single hand. The manipulation implies here the arming of the cannula, the arming of the stylet and the release of the shot allowing for the sample to be taken.

Among the existing devices, which enable a manipulation with one single hand, one of them is described in the U.S. Pat. No. 7,153,275. This device is perfectly functional if it is manipulated in a correct way i.e. in most cases. However, it happens that certain bad manipulations cause problems. In particular when the arming of the cannula or of the stylet has not been achieved correctly, the shot can be released in an unintentional way. This can cause problems because a shot can be released in particular before the device is correctly placed near the organ of which one wishes to take a sample.

Another problem that has been encountered with this kind of device is due to the fact that in case of incorrect manipulation the arming mechanism and the shooting mechanism may become totally jammed, thus rendering the device unusable.

An additional problem can occur when a traction force is applied to the cannula or to the stylet. This can occur particularly while the biopsy gun is put in place to take a sample. In that case, the elements that enable to maintain the stylet and/or the cannula in the armed position can be released from their support and cause an unintentional shot.

This invention proposes to realize a tissue sampling device which has the advantages of the devices of the prior art i.e. it is possible to use this device with one hand. However, this device does not have the drawbacks of the systems of the prior art. Thus, even in case of bad manipulation, the shot is not released in an unintentional way. Moreover, the device cannot be jammed as a result of a bad manipulation.

Another advantage of the device of the invention relates to the fact that even in case of a relatively large stress applied to the needle, for instance while this needle is put in place to be used to take a sample, an unintentional shot cannot be triggered. This feature is obtained without increasing the strength necessary for arming the gun.

Furthermore, and especially in implementations of the invention wherein the sampling device may be a single-use sampling device, particularly the risk of jamming of the needle and/or the cannula individually or in relation to each other is reduced or eliminated. This is at least partly because the sampling device, and particularly the movable parts thereof e.g. the needle and the cannula, is then assembled correctly during manufacture leaving no risks of a user putting the parts together in the wrong manner as could very well be the case with re-useable sampling devices. In addition, a single-use device is also significantly less prone to risks of contamination, e.g. by bacteria on a user's hands.

Moreover, as a single-use sampling device may enable production tolerances different from those of a re-useable sampling device, it is in most cases less costly to manufacture than such re-useable sampling devices. Thereby, the improved security mechanisms against unintentional firing of the sampling device according to the different implementations of the invention may be particularly, but not exclusively, suitable for single-use sampling devices in order to meet any potential risks due to such different production tolerances as mentioned above.

DISCLOSURE OF THE INVENTION

The aim of the invention is reached by a sampling device as defined in the preamble and characterized in that at least one element among said retaining element of the cannula slider and said retaining element of the stylet slider comprises at least a hook arranged to cooperate with a retaining device of said hook, the sampling device further comprises unlocking means of said hook arranged to release said retaining element from the corresponding retaining device and the sampling device further comprises at least one locking element arranged to prevent said hook from being released from said corresponding retaining device when said locking element is in a locking position and to allow said hook to be released from said corresponding retaining device when said locking element is in a position allowing the shot.

According to the present invention, the device for taking samples comprises a needle formed by a cannula and a stylet. The cannula is integral with the cannula slider and the stylet is integral with a stylet slider. These sliders comprise retaining means enabling the sliders to be held in such a position that the stylet and/or the cannula are armed i.e. in a position ready for a shot for taking samples. According to the invention, a locking mechanism prevents the shot from being triggered as long as this locking mechanism is in a locking position.

The device of the invention prevents the unintentional triggering of a shot. Such an unintentional shot can occur in the devices of the prior art in particular when the arming of the cannula has not been made correctly or when a too large stress is applied on one of the sliders or on the needle for instance.

In the present invention, the biopsy gun can comprise at least two security systems. One of them prevents the involuntary displacement of the trigger releasing a shot. The other prevents an unintentional shot due to the wrong arming. For this scope, the mechanism for arming the cannula cooperates with a security mechanism. This cooperation provides a guarantee that if the security mechanism is not activated, the arming is not achieved. If the security mechanism is activated, an unintentional shot cannot occur. Thanks to this, there is no risk that a shot is released accidentally. A third security system is described in more detail below.

By virtue of the geometry of the device, the propulsion and retaining elements for the stylet and the cannula can be arranged symmetrically around a longitudinal axis materialized by the stylet. This ensures that there are few transversal forces. Such transversal forces have the effect of increasing the friction between the parts, of causing wear and of risks of rupture as well as of jamming. By suppressing these transversal forces, it is possible to use smaller springs as it is no longer necessary to fight against friction. The biopsy gun is thus easier to use since the arming is made easier. Moreover, the gun can be used more often since the jamming risk is reduced.

For a same arming force, the gun can have a higher shot speed than the prior art guns since a larger part of the available energy is used for the shot and not for overcoming frictions.

BRIEF DESCRIPTION OF THE DRAWINGS

This invention and its advantages will be better understood with reference to the enclosed drawings and to the detailed description of a particular embodiment, in which:

FIG. 2 shows a first embodiment of a detail of the device of the invention, in a locking position;

FIG. 3 represents the detail of FIG. 2, in a position allowing the shot;

FIG. 4 represents a second embodiment of a detail of the invention, in a locking position;

FIG. 5 represents the detail of the invention as shown in FIG. 4, in a position that allows a sampling shot;

FIG. 6 represents the detail of the invention as shown in FIGS. 4 and 5 when arming the device;

FIGS. 7 and 8 represent a third embodiment of a detail of the device of the invention, respectively in locking position and in a position allowing the shot.

BEST MODE FOR CARRYING OUT THE INVENTION

Figure 1:
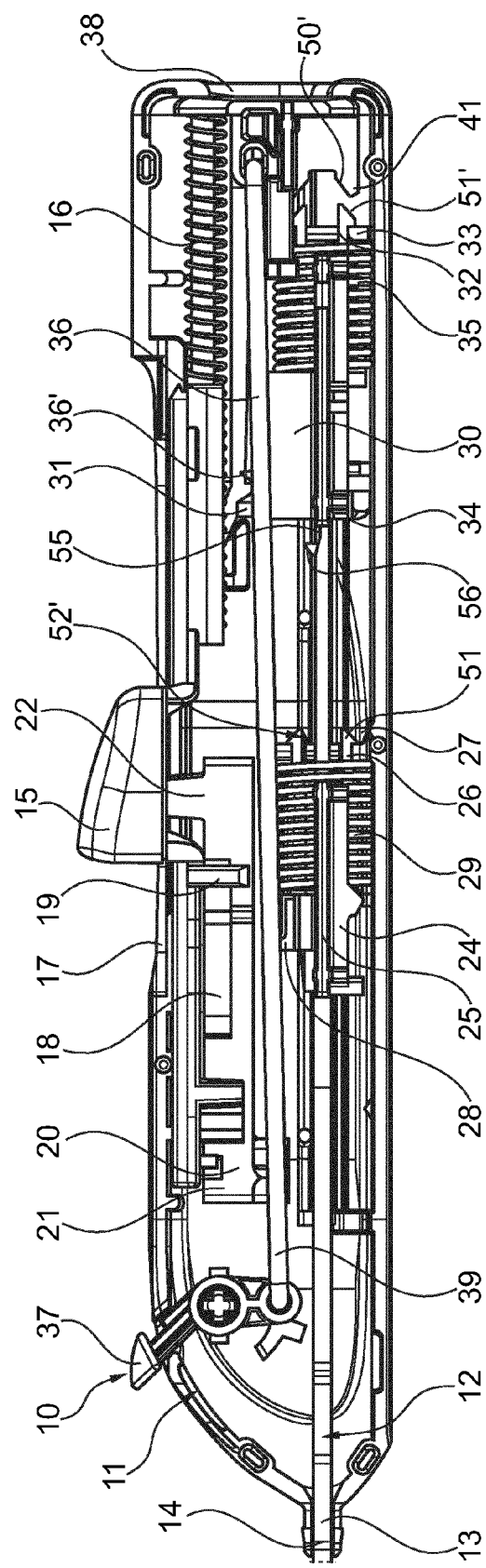
FIG. 1 is a sectional overview of the device for taking samples according to this invention.

FIG. 1 represents the device for taking samples 10 of the invention almost in its entirety. This device comprises a body 11 and a needle 12. The needle is formed by a stylet 13 and by a cannula 14. The stylet comprises a tip (not represented) allowing a penetration of the needle into the organ from which one wishes to take a sample. Furthermore, this stylet comprises at least one notch (not represented). In practice, the stylet 13 comprises a relatively long notch that enables a sample of great length to be taken. The cannula 14 slides around the stylet 13 and is used on one hand to section the tissue into which the stylet has penetrated and on the other hand to keep in place the tissues taken at the time of the extraction of the needle from the organ.

The body 11 essentially comprises an arming mechanism arranged to arm the needle 12 and a triggering device arranged to release a shot of the needle for the intended sampling. More particularly, the arming of the needle is carried out in two phases, namely a phase of arming the cannula 14 and a phase of arming the stylet 13.

The sampling is made by a shot of the needle. Such a shooting also comprises two phases, namely a displacement phase of the stylet 13 under the effect of a propelling power of the stylet, then a displacement phase of the cannula 14 under the effect of a propelling power of the cannula. Releasing a shot is achieved by liberating the displacement of the stylet. The displacement of the cannula is a consequence of the release of the stylet as it will be explained in detail below.

In practice, the mechanism for arming the cannula and the mechanism for arming the stylet use only one arming button 15 which acts differently depending on whether the arming of the cannula has already been carried out or not. This arming button cooperates with a return spring 16 of the arming button, this spring having the function to bring back the arming button 15 to the rest position i.e. towards the front of the body, when it is not manipulated.

The body of the device is formed by two parts which, once assembled, can comprise guidance grooves intended to ensure the displacement and the guidance of the parts. The body also comprises a slit 17 in which the arming button moves. It should be noted that further embodiments could be considered. For instance, the body can comprise one or more guidance surfaces or one or more rails arranged for cooperating with additional elements of the sliders in order to ensure guidance. According to another variant, it is possible to provide no rotational guidance of the mobile element.

The arming button 15 cooperates with a platform 18. This platform can pivot around a platform axis 19 integral with the arming button. One of the ends of the platform, located near the front end of the sampling device i.e. the needle-end of the sampling device, comprises a widened zone 20, each end of this widened zone including a finger 21 whose function is described in detail below. The rear end of the platform comprises a pushing device 22 whose function is also described in detail below.

The platform 18 is connected to the arming button 15 by the platform axis 19 and by a return device (not represented) that can be in particular a spring or an elastic tab and which has the function of keeping this platform in a predefined position called a rest position.

The mechanism for arming the cannula 14 is intended to move the cannula into the shooting position. This cannula is coupled to a cannula slider 24. According to one advantageous embodiment, the cannula slider 24 comprises two fins 25 disposed in a plane containing also the cannula. These two fins 25 cooperate with two guide grooves realized in the body of the device so as to ensure an effective sliding motion of the cannula slider 24. This slider comprises, at its rear end, a retaining element 26 of the cannula slider. According to an advantageous embodiment, the retaining element is formed by two hooks. Advantageously, these hooks are symmetrical and realized so as to have a certain flexibility, which allows for them to be hooked onto a retaining device 27 of the cannula slider and to be unhooked from this device by approaching the hooks to each other. It is also possible to use only one hook or several hooks arranged asymmetrically.

Furthermore, the cannula slider 24 comprises a spur 28 cooperating with one of the fingers 21 of the platform. The cannula slider cooperates with a spring 29 for the propulsion of the cannula slider, which is arranged between the cannula slider 24 and the retaining device 27 of the cannula slider. This spring 29 is designed to supply the required force to propel the cannula slider towards the front of the body. The displacement of the cannula slider towards the back of the body effects the compression of this spring.

The mechanism for arming the stylet is intended for the displacement of the stylet into the shooting position, this displacement being achieved after the cannula 14 has been armed. To that effect, the stylet 13 is coupled to a stylet slider 30, which comprises a spur 31 near its front end and a retaining element 32 at its rear end. Like for the cannula slider, the retaining element 32 can be formed by two partially elastic hooks. It can also be formed by only one hook or by several hooks arranged symmetrically or asymmetrically.

This retaining element 32 can be hooked on a retaining device 33 of the stylet slider and can be unhooked from this device by approaching the hooks to each other.

Like for the cannula slider, the hooks of the stylet slider are sufficiently flexible to be able to be deformed one towards the other and sufficiently rigid to be able to be maintained on an adequate support.

The stylet slider 30 comprises, at its front end i.e. at the side of the cannula slider 24, means for unlocking 34 the cannula slider formed for instance by two inclined planes. These unlocking means may comprise a striker 50 to allow the hooks 51 to be released from the corresponding holding element, this striker comprising for instance two inclined planes.

The stylet slider 30 cooperates with a spring 35 for the propulsion of the stylet slider, which is placed between the stylet slider 30 and the retaining device 33 of the stylet slider. This spring is designed to supply the required force to propel the stylet slider 30 towards the front of the body. The displacement of the stylet slider towards the back of the body effects the compression of this spring.

The device of the invention further comprises a security element 36 which can advantageously be formed by a security hook cooperating with a rear shoulder 36' of the stylet slider and with the spur 31 of this slider.

The device according to this invention further comprises a triggering device. According to an advantageous embodiment, this triggering device comprises two triggers 37, 38 connected together by a rod 39. One trigger 37 is placed in the front of the body, in front of the arming button 15 and the other trigger 38 is placed in the rear of the body. The rear trigger 38 is associated with a return spring of the trigger, designed to bring the trigger back in the original position after it has been pressed.

This enables the user to easily access the triggering mechanism, whatever the position of the hand when using the device.

The rear trigger 38 comprises means for unlocking 41 the stylet slider. These unlocking means may comprise a striker 50' allowing the hooks 51' to be released from the corresponding holding element, this striker including for instance two elements arranged in inclined planes.

With reference to FIGS. 2 to 10, at least one of the hooks 50, 50' of the sliders, either the stylet slider 30 or the cannula slider 24, cooperates with a locking element of this hook. The function of this locking element is to maintain the hook against the corresponding retaining device 26, 33 when the device is not used for carrying out a sampling shot.

The locking element can be in a locking position in which it maintains at least one hook against the retaining device of the corresponding slider and a position allowing the shot. This position enabling the shot allows the hooks to be released from the corresponding retaining device. The change from one position to the other can be achieved in a fully manual, partially manual and partially automatic or fully automatic way.

In case of fully manual change of position, the user acts on the locking element during each change of position of this locking element. For arming the sampling device, the locking element must be positioned in the position allowing the shot. When the arming of one of the sliders is achieved, the corresponding locking element has to be positioned in the locking position. This locking element has to be positioned in the position allowing the shot before carrying out a sampling shot. When both the cannula slider and the stylet slider cooperate with a locking element, the same operation is carried out by both locking elements. When a shot is ready to be carried out, it is important for the locking elements to be in the position allowing the shot. It is also possible that a single manipulation positions all the locking elements in the position allowing the shot.

In case of partially manual and partially automatic change of position of the locking element, it is possible to automatically place the locking element or locking elements in locking position when the arming of the device is achieved. The user can manually achieve the displacement into a position allowing the shot when he/she is ready to carry out a sampling shot.

In the fully automatic operating mode, the user does not manipulate the locking element or the locking elements. In this case, several configurations are possible. If only one locking element is provided, the latter can be placed for cooperating either with the cannula slider or with the stylet slider. The locking element can be moved from the locking position into the position allowing the shot, for instance during the shot or just before this. This displacement can be carried out for instance by activating a trigger which action also involves triggering the shot.

Other variants are described in more detail with reference to FIGS. 2 to 10.

FIGS. 2 and 3 illustrate a first embodiment of a locking element 52 usable in a sampling device according to this invention. In this embodiment, the locking element includes at least a finger 53 integral with the striker 50. More specifically, in the illustrated embodiment, the locking element includes as many fingers as there are hooks 51 on the corresponding slider. When the striker is in a backward position, the fingers 53 of the locking element maintain the hooks against the retaining device 27, 33 of the corresponding slider. These fingers prevent the hooks to be unhooked from the corresponding retaining device and the locking element is in the locking position. This is shown in FIG. 2.

When a sampling shot has to be carried out, the striker 50 is moved forward under the action of a force applied to this striker. When the concerned locking element 52 acts on the hooks of the cannula slider 24, the striker is moved forward under the action of the force driving the stylet slider 30. When the concerned locking element acts on the hooks of the stylet slider 30, the striker is moved forward under the action of a force allowing the release of the stylet slider. Details of such release of the stylet slider are given hereafter. According to a preferred embodiment, the force for releasing the stylet slider is applied by the rear trigger 38.

Since the fingers 53 of the locking element 52 are integral with the striker, these fingers also move towards and away from the hook. This is shown in FIG. 3. At this point, the hooks can be released from the corresponding holding element and the shot can be carried out. In this position, the locking element 52 is in the position allowing the shot. The displacement of the locking element is fully automatic since it is linked to the arming of the sliders and to the shot. No additional or specific manipulation should be made to change the position of the locking element.

The embodiment shown in FIGS. 4 to 6 comprises a locking element 52' made in form of a tongue 54 cooperating with a drive rod 55. The tongue 54 is integral with one of the hooks of the cannula slider 24 or of the stylet slider 30. It should be noted that it is also possible to use such tongue on several hooks, even on all the hooks of one or both sliders.

This tongue can pivot about its connection area with the hook. In the absence of stress, the tongue 54 is in a position in which the free end is directed to the front of the sampling device. This position of the tongue is shown in FIG. 1.

Assuming that the locking element 52' is placed on a single hook 51 of the cannula slider 24 only, the operation of the sampling device is as follows. In a rest position, both sliders are located towards the front of the device. The tongue 54 is inclined forward, which means that its free end is directed towards the front of the device.

When the arming button 15 is activated for the first time, the cannula slider 24 is driven towards the rear. The tongue 54 exceeds the drive rod 55 without interfering with the latter or whilst bending slightly. The hooks 51 are located on the retaining device 27 of the cannula slider and hold this slider in place. This position is shown in FIG. 4.

When the arming button 15 is activated again, the stylet slider 30 is moved towards the rear. This stylet slider is integral with the drive rod 55. The drive rod comprises a shoulder 56 that cooperates with the tongue 54 during the arming of the stylet slider. Due to the respective size and positions of the tongue and of the drive rod, at the end of the stroke of the stylet slider 30, the tongue 54 rests against the drive rod 55 and prevents the hook 51 to be released from the retaining device 27. This is shown in FIG. 5. In this position, the locking element 52' is in a locking position and the hooks cannot be released from the corresponding retaining device.

When a shot is carried out, the stylet slider 30 is activated as described with more details below. As a result the drive rod 55 is moved forward and is therefore no longer in contact with the tongue 54. The unlocking means release the cannula slider 24. During the shot, the tongue 54 is pivoted towards the rear under the action of the drive rod 55. In this position, shown in FIG. 6, the tongue does not interfere with the displacement of the slider. At the end of the shot, the tongue returns to its natural position, i.e. inclined to the front of the device. The displacement of the locking element 52' from a locking position into a position allowing the shot is automatic in that the user does not have to carry out any specific manipulation for changing this position. He/she manipulates the device in a conventional way.

With reference to FIGS. 7 and 8, the locking element 52" comprises a cam 60 arranged near one of the hooks 51, 51' of the cannula slider 24 and/or of the stylet slider 30. According to an advantageous embodiment, the cam 60 has an elliptical shape. As explained previously, the locking element 52" is mobile between two positions, namely a locking position and a position allowing the shot. The locking position is shown in FIG. 7. In this position, an area of the cam rests against one of the hooks and prevents the latter to be unhooked from the corresponding retaining device. Thus, if the striker 50, 50' rests against the hooks in an unintentional way, these cannot be released since these are locked by cam 60.

The position of the cam allowing the shot is shown in FIG. 8. In this position, the minor axis of the ellipse is directed towards the hook. The hook and the cam are sized in such a way that when the cam is in its position allowing the shot, the hook can move towards the centre of the retaining device and be released from this element.

When the cam 60 is in this position, if the striker 50, 50' comes into contact with the hooks, it can release them from the corresponding retaining device without these hooks interfering with the cam. Therefore, these can be released and the sampling shot can be carried out.

Before arming the device, the cam is in the position allowing the shot. During the arming of the gun, the cam 60 is pivoted at the end of the arming, so as to be in the locking position and thus to ensure that the hooks cannot be released from the holding element. A lever acting on the cam can generate this rotation of the cam just after the hooks exceeded the corresponding retaining device. This rotation can be generated by the same displacement than the one that slightly moves back the stylet slider at the end of the arming of the cannula slider.

The inverted displacement of the locking element i.e. its displacement from the locking position into the position allowing the shot can advantageously be carried out by means of a rod linked to a trigger used for triggering a sampling shot, for instance the rear trigger 38. Thus, when the device is armed, it is in a locked position, without any manual intervention of the user. When a user triggers a shot, the shot triggering causes the cam to rotate into the position allowing the shot.

It should be noted that the cam 60 could also be pivoted in a manual or partially manual way. In case of manual rotation of the locking element, a button accessible from the exterior of the housing is provided for rotating the cam. In case of partially manual and partially automatic rotation, the cam can take for instance its locking position in an automatic way during the arming of the device. The change of position from the locking position into the position allowing the shot could be carried out manually, by pressing a button accessible from the exterior of the housing or automatically, for instance by means of a rod that connects the cam to the rear trigger.

Figure 9:
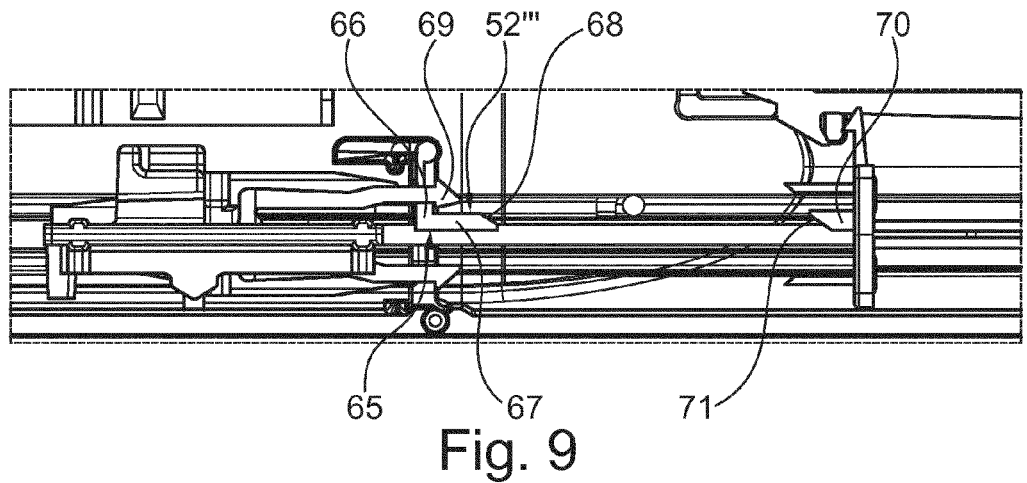
FIGS. 9 and 10 represent a fourth embodiment of a detail of the device of the invention, respectively in a locking position and in a position allowing the shot.
Figure 10:
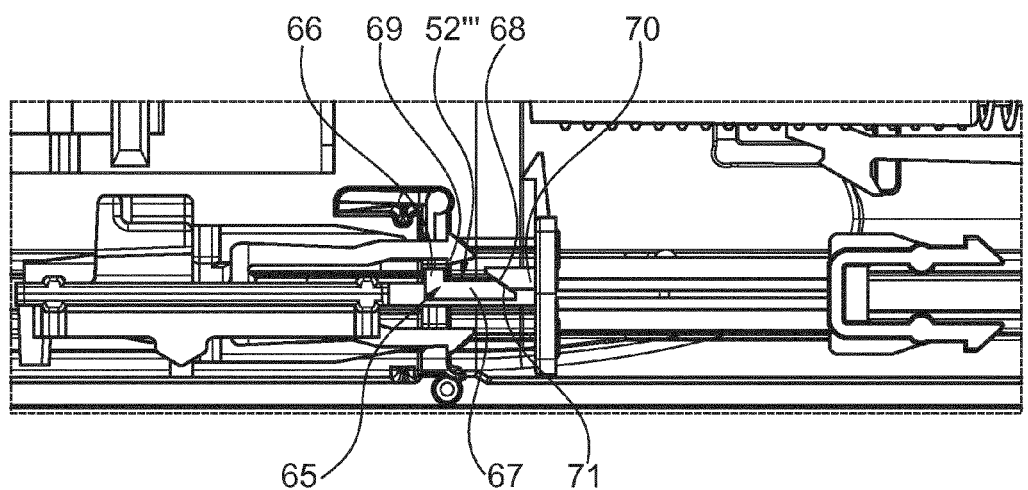

According to an embodiment shown in FIGS. 9 and 10, the locking element 52''' comprises a finger 65 which is mobile between a locking position and a position allowing the shot. More specifically, this finger is mobile in a plane perpendicular to a longitudinal axis of the device formed by the needle. The finger has essentially a set square form, a branch 66 of this finger being arranged for being placed near one of the hooks 51, 51' of one of the sliders 24, 30 and the other branch 67 of this set square including at its end, an inclined area 68.

The locking element 52''' is associated to a spring (not represented) that presses the finger towards the hook when no further stress is applied to this finger. The hook includes a shoulder 69 arranged to rest against the finger, which reinforces the maintenance of the hook on the corresponding retaining device.

The finger cooperates with a drive rod 70 associated to the striker 50. This drive rod has an end comprising an inclined plane 71 that cooperates with the inclined area 68 formed on the longitudinal branch 67 of the finger 65. As a result of the displacement of the drive rod towards the front of the sampling device, the inclined plane 71 of this drive rod comes into contact with the inclined area 68 of the finger, the force applied by this drive rod overcoming the force of the finger spring in order to move away the finger from the hook. This allows the striker 50, 50' to press the hooks 51, 51' towards the centre of the corresponding retaining device 27, 33 and thus to release the hooks. When the drive rod is released, the spring moves the finger towards the hook and thus locks the latter in locking position.

During the arming of the device, the form of the hook allows the spring to be forced and to move the finger 65 downwards, which allows the hooks to be positioned on the corresponding retaining device.

If the locking element 52''' is formed on the cannula slider 24, the drive rod 70 can be connected to the stylet slider 30. If the locking element is provided on the stylet slider 30 the drive rod can be connected to the trigger 38 used for triggering a sampling shot.

It should be noted that usually, it is advantageous for the hooks to be symmetrical, so as to limit twists in the device of the invention. However, it is not necessary to make locking elements for all the hooks. Indeed, if only one of the hooks cannot be released from the corresponding retaining device, the whole slider will be locked. Setting up a locking element on all the hooks is however possible.

The sampling device according to this invention operates in the following way. Let us assume that the initial position is a position in which the cannula 14 and the stylet 13 are maximally extended towards the outside of the body 11 of the device. This position corresponds to the normal position of the device when it is not going to be used, i.e. rest position. This position is shown in FIG. 1.

In a first phase, the arming of the cannula 14 is carried out. During this operation, the user actuates the arming button 15, making it slide towards the back of the device 10. The platform 18 being integral with the arming button 15, the displacement of the latter also draws the platform backwards. One of the fingers 21 of the platform 18 comes in contact with the spur 28 placed towards the front end of the cannula slider 24. The latter is thus displaced backwards, in opposition to the force of the spring 29 for the propulsion of the cannula slider. This movement is carried out until the retaining elements 26 of the cannula slider 24 enter into contact with the retaining device 27 of the cannula slider. This retaining device 27 is for instance a ring realized in the body of the device. The ring comprises a central hole in which the ends of the hooks of the cannula slider pass. These hooks lean on the back face of the ring and maintain the cannula slider 24 in opposition to the force of the propulsion spring of this cannula slider. During the arming of the cannula slider, the locking element should not prevent the positioning of the hooks. If the change of position of the locking element is manual and if a locking element is provided to cooperate with the cannula slider, it is necessary to place this locking element in the position allowing the shot before the arming of the cannula.

In the embodiment wherein the change of position is automatic, the position of the locking element is such that the arming of the cannula is possible.

According to an advantageous embodiment, at the end of the stroke of the platform i.e. just before the retaining elements 26 of the cannula slider are maintained by the corresponding retaining device 27, the platform 18 comes in contact with the spur 31 of the stylet slider and displaces the latter slightly backwards. Following this displacement, the hook forming the security element 36 cooperates with the rear shoulder 36' of the stylet slider and retains this slider in this position by preventing it from moving forward.

The end of the stroke of the platform also has the effect of displacing the cannula slider 24 into a position such that the retaining element 26 of the cannula slider is maintained on the retaining device 27 of the cannula slider.

When the stylet slider 30 is retained by the security hook, the unlocking means 34 being part of the stylet slider 30 or in other words, the means for unlocking the cannula slider, cannot move sufficiently forward to separate the hooks of the cannula slider from the retaining organs 27 of these hooks. In this way, if the arming of the cannula is not carried out beforehand, the hooks of the cannula slider do not hook to the corresponding retaining device, which is immediately detected by the user who simply needs to restart the arming of this cannula. If the arming of the cannula has been carried out correctly, the hooks of the retaining device are maintained in place and the hook of the security element 36 cooperates with the stylet slider 30 so as to prevent from advancing beyond a predetermined position. In this way, an unintentional release of the shot is not possible.

When the arming of the cannula is terminated, the arming button 15 is released. It returns to its initial position towards the front of the device, under the effect of the return spring 16 of the arming button.

During the forward displacement of the platform 18, following the forward displacement of the arming button 15, a ramp of the platform comes into contact with a plug realized in the body. This ramp has the effect of rotating the platform 18 around the platform axis 19, against the force of the return device of the platform. It should be noted that according to the chosen practical realization, it is also possible to provide for the return device of the platform to be constrained before the arming of the cannula and to be liberated when the arming of the cannula is terminated.

For the arming of the stylet 13, the arming button 15 is displaced backwards again. However, the platform 18 is no longer in the initial position. Indeed, the latter has pivoted around the platform axis 19, as the ramp of the platform has been displaced by the support against the plug. By this rotation, on one side the finger 21 of the platform does not come into contact with the spur 28 of the cannula slider and on the other side, the pushing device 22 of the platform leans against the spur 31 of the stylet slider. In a first stage, the pushing device 22 is placed next to the spur 31 while in a second stage, the pushing device 22 rests against the spur 31.

The stylet slider is thus displaced towards the back of the device, in opposition to the force of the propulsion spring 35 of the stylet slider, until the retaining elements 32 of the stylet slider are placed in the retaining device 33 of the stylet slider. This retaining device is similar to the retaining device 27 of the hooks of the cannula slider. It has thus advantageously an annular form with a hole into which the hooks of the stylet slider fit. As in the case of arming the stylet slider, the locking element, if such a locking element is provided to cooperate with the stylet slider, must also be in a position allowing the arming of the stylet. This position can be reached in an automatic, manual or partially manual and partially automatic way according to the selected embodiment.

It should be noted that a locking element could be intended to cooperate only with the stylet slider, and only with the cannula slider or with both sliders. If a locking element is provided for both sliders, the fully manual, entirely automatic or partially manual and partially automatic displacement mode of the locking elements can be selected in an independent way for each of the sliders.

At this stage, the device is triggered out and ready for the shot. The device is stable in the sense that the cannula and stylet slider hooks are maintained against the corresponding retaining elements. The hook of the security element 36 is no longer in contact with the rear shoulder 36' of the stylet slider. The arming button 15 is released and returns to its initial position under the effect of the return spring of the arming button. The platform 18 also returns to its initial position.

If the arming of the stylet is not carried out correctly and the hooks of the cannula slider are not well maintained on the corresponding retaining device, the stylet slider moves in direction of the cannula slider. The security element 36 cooperating with the rear shoulder 36' of the stylet slider prevents the unlocking means 34 connected to this stylet slider (or means for unlocking of the cannula slider) from interacting with the retaining element 26 of the cannula slider. Thus, even in case of bad manipulation during the arming of the stylet, an unintentional shot cannot be released. Moreover, the locking element(s) also prevent(s) the hooks to be released from the corresponding retaining device, which further improves security against unintentional shots.

When the needle is armed, the sampling is started by a shot. This shot can be started by means of one of the triggers 37, 38. According to an advantageous embodiment, a security mechanism is provided for preventing a shot during an involuntary manipulation of one of the triggers and in particular of the front trigger. Before the release of the shot, it is necessary to laterally displace this front trigger 37 relative to the body 11 in order to remove the security function of the mechanism. After the shot, it is necessary to laterally re-displace the front trigger 37 in order to reactivate the security function. This security is manual in the sense that the user has the choice to activate the function by displacing the trigger, or not to activate it.

To release the shot, it is necessary to press one of the triggers 37, 38, the front or the rear one. Actually, in the disclosed embodiment, the shot is always released by a displacement of the rear trigger 38. However, the front trigger and the rear trigger being linked by the rod 39, a pressure on the front trigger has as result to move the rear trigger forward under the pressure of the rod. Thus the mechanism can be used by pressing either the rear trigger or the front trigger. When a locking element has to be manually activated for reaching its position allowing the shot, this displacement must be carried out at this stage.

When the rear trigger 38 is pressed, the unlocking means 41 being part of the rear trigger (or means for unlocking the stylet slider) comes into contact with the hooks of the stylet slider and displaces them towards each other. In this way, they are released from the retaining device 33 of the stylet slider. This slider 30 is propelled forward under the effect of the propulsion spring 35 of the stylet slider. Depending on the selected embodiment, the displacement of the rear trigger also activates the locking element or at least one of the locking elements and drives it in a position allowing the shot.

As the hook of the security element 36 is integral with the rear trigger 38, the fact of displacing this trigger forward also has the effect of displacing the security hook forward and upward. Thus the stylet slider 30 is no longer retained by this hook and can advance far enough so that the unlocking means 34 being part of this stylet slider, come into contact with the hooks 26 of the cannula slider 24.

The means 34 for unlocking the cannula slider (or the striker 50 of such unlocking means) comes into contact with the hooks of the cannula slider, presses these hooks towards the centre and releases the retaining elements 27 of the cannula slider. The cannula slider 24 advances under the effect of the propulsion spring 29 of the cannula. This slider advances until it arrives at a stop realized in the body of the device. At this stage, the shot is terminated and the device can be withdrawn from the organ from which samples have been taken.

After the arming of the stylet, the platform 18 has returned to its rest position under the effect of the return device of the platform. After the shot, the pieces composing the device return to their initial positions. The sample taken is confined between the stylet 13 and the cannula 14, in the notch provided for this purpose. This sample can be withdrawn by moving back the cannula, for instance by carrying out an arming movement as previously explained. When the arming of the cannula is terminated, it is possible to withdraw the sample without any risk because an unintentional shot is not possible. If a new sampling has to be carried out, the arming button is operated so as to arm the device totally and to make it ready for the shot. If it is not necessary to take a new sample, the arming is carried out as well and a blank shot is made.

The present invention has several advantages in comparison with the devices of the prior art. In particular, by the setup of the retaining elements 26, 32 of the stylet and cannula sliders, it is possible to provide at least two symmetrical hooks. The forces applied on these hooks to hold them by the retaining means as well as during their unhooking during a shot are symmetrical. On one hand, this ensures that there is no flexing and/or twist on the needle and on the other hand, this enables a safer support of the hooks.

According to an advantageous realization, the needle is off-center towards the bottom of the device 10. This enables the use of the device in an easier way with another apparatus as for example an echographic probe.

In case of incomplete movement during the arming of the cannula, the hooks of the cannula slider are simply not maintained on the corresponding retaining device. This has the advantage that an unintentional shot is not possible and that the arming of the stylet is not possible if the arming of the cannula is not done correctly.

The locking element(s) further improve(s) security against unintentional shots by locking the hooks against the corresponding retaining devices before a sampling shot.

The device according to the invention can be operated by one single hand since the arming of the cannula and the arming of the stylet use the same arming button.

By the symmetrical construction of the retaining elements of cannula and stylet sliders and by the position of the propulsion springs of these sliders, the stresses are divided symmetrically around the axis of the needle. Thus, the risks of jamming between the stylet and the cannula are minimized, which in some implementations of the invention enables the use of the device several times and thus allows for a greater number of samples to be taken.

The reduction of the jamming risk allows for the reduction of the force of the propulsion springs while maintaining a high displacement speed for the sliders. This is advantageous for the user because a smaller force is necessary for arming the device. The manipulation with a single hand is easier in this way.

Using guide grooves realized in the body of the device and slider fins moving in these grooves also ensures an optimal guidance and a diminution of the jamming risk.

The invention claimed is:

1. A sampling device for taking a sample of soft tissue from an organ, the sampling device comprising:
    a body and a needle oriented on a longitudinal axis of the body and of the sampling device, the needle formed by a stylet and a cannula coaxial with the stylet;
    an arming button for arming the needle, the arming button connected to a platform provided with a platform finger and a platform pusher, the platform finger to engage a cannula slider of the cannula and adapted to move the cannula to a shooting position, the platform is rotatable on a platform axis to a rotated position that engages the platform pusher with a stylet slider of the stylet such that subsequent movement of the platform pusher moves the stylet to the shooting position, wherein the stylet and the cannula are retained in the shooting position with the stylet and the cannula retracted into the body of the sampling device;
    at least one trigger adapted to release the stylet and the cannula from the shooting position;
    the cannula being coupled kinematically to the cannula slider, the cannula slider comprising at least one cannula retaining element for retaining the cannula slider in the shooting position and the stylet being coupled kinematically to the stylet slider, the stylet slider comprising at least one stylet retaining element for retaining the stylet slider in the shooting position and a striker for unlocking the cannula slider, the striker located inferior relative to the arming button, characterized in that at least one of the at least one cannula retaining element and the at least one stylet retaining element comprises at least one hook arranged for cooperating with a corresponding retaining device, the sampling device further comprising at least one locking element arranged to contact the at least one hook to prevent the at least one hook from being released from the corresponding retaining device when the locking element is in a locking position and arranged to allow the at least one hook to be released from the corresponding retaining device when the locking element is in a position allowing a shot.

2. The sampling device according to claim 1, wherein the locking element is integral with at least one of the striker and a second striker for unlocking the stylet slider.

3. The sampling device according to claim 2, wherein the locking element comprises at least one finger arranged to hold the at least one hook between the corresponding retaining device and the finger when the locking element is in the locking position and to free a passage between the finger and the corresponding retaining device when the locking element is in the position allowing the shot.

4. The sampling device according to claim 1, wherein the locking element is integral with the at least one hook.

5. The sampling device according to claim 4, wherein the locking element comprises a tongue pivoting on the at least one hook, the tongue being mobile between a first position in which a free end of this tongue is inclined towards a front of the device, a second position called locking position in which the free end of the tongue rests against a drive rod and a third position in which the free end of the tongue is inclined towards a rear of the device.

6. The sampling device according to claim 5, wherein the tongue is integral with the at least one hook of the cannula slider and the drive rod is integral with the stylet slider.

7. The sampling device according to claim 5, wherein the tongue is integral with the at least one hook of the stylet slider and the drive rod is integral with a second striker for triggering a shot of the stylet slider.

8. The sampling device according to claim 5, wherein the tongue is in the first position in the absence of stress on this tongue.

9. The sampling device according to claim 5, wherein the drive rod comprises a shoulder arranged for displacing the tongue from the first position into the second position.

10. The sampling device according to claim 1, wherein the locking element comprises a cam mobile between a locking position in which the at least one hook is held between the corresponding retaining device and the cam, and a position allowing the shot in which the cam is moved away from the at least one hook.

11. The sampling device according to claim 10, wherein the cam rotates about an axis integral with a housing of the sampling device.

12. The sampling device according to claim 11, wherein the cam is manually rotated.

13. The sampling device according to claim 11, wherein the cam comprises a cam stem arranged for rotating the cam during the arming of the device and during a sampling shot.

14. The sampling device according to claim 13, wherein the cam stem is at least one of connected to the stylet slider and connected to a second striker for triggering a shot of the stylet slider.

15. The sampling device according to claim 1, wherein platform finger is mobile along one axis which is perpendicular to the longitudinal axis and the device further comprises a drive rod acting on the finger for displacement of the finger.

16. The sampling device according to claim 15, wherein the platform finger comprises an inclined area cooperating with an inclined plane formed on the drive rod.

17. The sampling device according to claim 15, wherein the platform finger is forced into the locking position by a locking spring.

18. The sampling device according to claim 15, wherein the platform finger cooperates with the cannula slider and the drive rod is integral with the stylet slider.

19. The sampling device according to claim 15, wherein the platform finger cooperates with the stylet slider and the drive rod is integral with a second striker for triggering a shot of the stylet slider.

* * * * *

UNITED STATES PATENT AND TRADEMARK OFFICE
CERTIFICATE OF CORRECTION

PATENT NO. : 9,888,908 B2
APPLICATION NO. : 14/369201
DATED : February 13, 2018
INVENTOR(S) : David Callede et al.

It is certified that error appears in the above-identified patent and that said Letters Patent is hereby corrected as shown below:

Claim 15 at Column 14, Line 2 "-- platform finger is mobile --" should read "-- the platform finger is mobile --"

Signed and Sealed this
Twenty-fifth Day of December, 2018

Andrei Iancu
*Director of the United States Patent and Trademark Office*